United States Patent
Renna et al.

(10) Patent No.: US 9,658,158 B2
(45) Date of Patent: May 23, 2017

(54) DIAGNOSTIC DEVICE WITH INTEGRATED PHOTODETECTOR, AND DIAGNOSTIC SYSTEM INCLUDING THE SAME

(71) Applicant: STMICROELECTRONICS S.R.L., Agrate Brianza (IT)

(72) Inventors: Lucio Renna, Acireale (IT); Clelia Carmen Galati, San Gregorio di Catania (IT); Natalia Maria Rita Spinella, Paterno (IT); Piero Giorgio Fallica, Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 1027 days.

(21) Appl. No.: 13/902,468

(22) Filed: May 24, 2013

(65) Prior Publication Data
US 2013/0330836 A1 Dec. 12, 2013

(30) Foreign Application Priority Data
Jun. 8, 2012 (IT) ............................. TO2012A0501

(51) Int. Cl.
*G01N 33/551* (2006.01)
*G01N 21/64* (2006.01)

(52) U.S. Cl.
CPC ..... *G01N 21/6428* (2013.01); *G01N 21/6454* (2013.01); *G01N 33/551* (2013.01)

(58) Field of Classification Search
None
See application file for complete search history.

(56) References Cited

U.S. PATENT DOCUMENTS

| | | | | |
|---|---|---|---|---|
| 7,586,603 B2 * | 9/2009 | Maity | ...................... | G01J 1/44 356/301 |
| 7,768,650 B2 * | 8/2010 | Bazylenko | ........... | G01N 21/253 356/491 |
| 8,476,730 B2 * | 7/2013 | Sanfilippo | ......... | H01L 31/02241 257/428 |
| 9,209,336 B2 * | 12/2015 | Sanfilippo | ......... | H01L 27/14643 |
| 9,349,904 B2 * | 5/2016 | Russo | ................ | G01N 21/6454 |

(Continued)

FOREIGN PATENT DOCUMENTS

WO 2007/144864 A1 12/2007

OTHER PUBLICATIONS

Search Report and Written Opinion, dated Feb. 19, 2013, from IT TO20120501.

*Primary Examiner* — Chris L Chin
(74) *Attorney, Agent, or Firm* — Seed IP Law Group LLP (57) ABSTRACT

A diagnostic device includes a photodiode formed by a body of semiconductor material having a first surface, an integrated optical structure on the first surface and having a second surface, and at least one detection region on the second surface. The at least one detection region includes at least one receptor that binds to a corresponding target molecule that can be mated with a corresponding marker, which, when excited by radiation having a first wavelength, emits radiation having a second wavelength that can be detected by the photodiode. The integrated optical structure includes at least a first layer of a first material having a first refractive index. The first layer has a thickness substantially equal to an integer and odd multiple of one fourth of the first wavelength divided by the first refractive index.

21 Claims, 8 Drawing Sheets

(56) References Cited

U.S. PATENT DOCUMENTS

| | | | |
|---|---|---|---|
| 2009/0017553 A1 | 1/2009 | Hoying et al. | |
| 2009/0184384 A1* | 7/2009 | Sanfilippo | H01L 27/14643 |
| | | | 257/432 |
| 2011/0291026 A1 | 12/2011 | Renna et al. | |

* cited by examiner

DIAGNOSTIC DEVICE WITH INTEGRATED PHOTODETECTOR, AND DIAGNOSTIC SYSTEM INCLUDING THE SAME

BACKGROUND

The present invention relates to a diagnostic device with integrated photodetector, and to a diagnostic system including said diagnostic device.

As is known, available today are numerous diagnostic devices for biological applications.

In general, diagnostic devices each include a respective assay. In turn, the assay may comprise a solid substrate, which is typically of a flat type and has a surface functionalized so as to present detection regions, inside which receptors, which are provided with specific markers, are immobilized.

In practice, by "receptor" is meant any member of a pair or of an N-tuple of elements that can bind together. Consequently, each receptor is able to mate, or in any case react, with a respective binding mate, or else with a respective plurality of binding mates, enabling detection thereof. For example, receptors can comprise biomolecules (DNA, RNA, proteins, antigens, antibodies, haptens, sugars, etc.) or chemical species, or micro-organisms or parts thereof (bacteria, viruses, spores, cells, etc.). Binding mates are also known as "targets" or "target molecules"; moreover, receptors are also known as "probes" or "probe molecules".

As regards markers, each one of them is such that, when the corresponding receptor mates or interacts with its own binding mate, or binding mates, it can be activated, i.e., it can mate with the receptor by mating with the binding mate. Given any receptor, it is hence found that, when it is in direct contact with a specimen to be analysed, present inside which are binding mates that are able to mate/interact with the receptor, the corresponding markers can be activated.

In particular, in so-called fluorescence diagnostic devices, an activated marker, if excited with a light radiation at a certain wavelength $\lambda_e$, emits a light radiation of its own having a wavelength $\lambda_f$ longer than the wavelength $\lambda_e$. In general, said markers are known as "fluorescence markers".

This being said, there are known, among other things, the so-called "three-component binding assays", which each use a first immobilization of a first antibody on a solid substrate, said first antibody being able to mate with an antigen present in a standard solution. Binding with the antigen is then detected thanks to a second antibody, which functions as marker and binds to an epitope of the antigen itself. The second antibody has a fluorescent label attached to it; consequently, the amount of fluorescence is correlated to the amount of antigens present in the standard solution.

In practice, by detecting the light radiation at the wavelength $\lambda_f$, information regarding the chemico-physical characteristics of the specimen to be analysed may be inferred since the light intensity detected is a function of the amount of activated markers in the assay, and hence of the amount of molecules or biomolecules detected by the assay. For this purpose, the optical detector is sensitive to the wavelength $\lambda_f$ of the light radiation emitted by the markers.

In greater detail, in order to detect the light radiation emitted by the markers, there is known the use of optical detectors, which enable scanning of small portions of specimens to be analysed in order to determine characteristics and/or properties of the specimens. These optical detectors usually comprise optical elements and movement devices having particularly small dimensions, for example in the region of a few millimeters. In addition, optical detectors are known in which the movement devices are formed by micro-electromechanical systems (MEMS).

Irrespective of the details of implementation, typically a generic optical detector is coupled to a corresponding diagnostic device, set inside which is at least one specimen to be analysed in such a way that, by illuminating with a first beam of light at least one portion of the specimen, the optical receptor receives a second beam of light coming from the specimen itself and generated, in the case of a fluorescence diagnostic device, by excitation of the specimen by means of incidence of the first beam of light.

In order to increase the capacity of analysis and, in particular, to be able to detect ever more limited amounts of activated markers, it is desirable to maximize the light intensity of the beam emitted by fluorescence and/or increase the sensitivity of the optical detector.

By way of example, the patent application No. TO2010A000437 filed on May 25, 2010 in the name of the present applicant describes an optically accessible microfluidic diagnostic device, which can hence be coupled to an optical detector.

The diagnostic device comprises a substrate of semiconductor material, overlaid by a compatible layer, made, for example, of silicon dioxide ($SiO_2$).

The diagnostic device described in the patent application No. TO2010A000437 further comprises a structural layer, formed, for example, by a photoresist and arranged on top of the compatible layer, with which it is in direct contact. Formed within the structural layer are one or more channels, obtained by means of selective removal of one or more portions of the structural layer, until the underlying compatible layer is reached and exposed. The bottom of each channel is hence delimited by the compatible layer, whilst the side walls are delimited by the structural layer. Each channel houses one or more detection regions, where receptor biomolecules are present, deposited for example by means of the so-called "automated spotting technique". The detection regions are hence formed by drops of biological material, said drops having dimensions comprised between a few picoliters and a few microliters. Access to each channel and to the corresponding detection regions is provided by a corresponding inlet hole and by a corresponding outlet hole, which extend through the substrate and the compatible layer. With regard to the compatible layer, it is in fact defined "compatible" because it does not interfere with the detection regions, and in particular with the receptors present therein. Optionally, the compatible layer can be replaced by a non-compatible layer, provided that it is appropriately passivated. Moreover, the compatible layer can be functionalized, for example by means of addition of hydroxyl groups (OH groups) in order to enable immobilization of the receptors.

The diagnostic device described in the patent application No. TO2010A000437 further comprises a cover layer, formed by an adhesive film and laid on the structural layer, with which it is in direct contact so as to seal the channels at the top. In use, the excitation radiation is generated above the cover layer and impinges upon the detection regions after traversing the cover layer. The fluorescence radiation, generated by the excited markers, is in turn detected by means of a photodetector set on top of the cover layer, hence after prior traversal of the cover layer, which is hence transparent both to the wavelength $\lambda_e$ and to the wavelength $\lambda_f$.

The compatible layer is also transparent to the wavelength $\lambda_e$ and to the wavelength $\lambda_f$. Furthermore, in order to increase the light intensity of the beam emitted by fluorescence, the thickness of the compatible layer is sized in such a way that the corresponding optical thickness is substantially equal to an integer and odd multiple of the wavelength $\lambda_e$ of the excitation radiation, the direction of incidence of which on the compatible layer is assumed as being orthogonal to said layer. In this way, thanks to phenomena of constructive interference, there is an increase of the electrical field associated to the excitation radiation in the detection regions and, consequently, a maximization of the light radiation emitted by the excited markers.

Even though the geometry adopted in the patent application No. TO2010A000437 envisages that the optical source, which generates the excitation radiation, and the optical detector are set on one and the same side with respect to the channel, and hence with respect to the assay, there are also known diagnostic systems that adopt different geometries.

For example, diagnostic devices are known of the type described in the patent application No. WO2007/144864, where a detection region is present, which is carried by a support and is set between the optical source and the optical detector.

Furthermore, according to the patent application No. WO2007/144864, the optical detector is a Geiger-mode avalanche photodiode (GM-APD), also known as single-photon avalanche diode (SPAD) in so far as it is able to detect single photons.

In general, a SPAD is formed by an avalanche photodiode and hence comprises a junction, typically of P+/N type, or else an N+/P junction.

In greater detail, the junction has a breakdown voltage $V_B$ and is biased, in use, with a reverse-biasing voltage $V_A$ higher in modulus than the breakdown voltage $V_B$ of the junction, typically 10-20% higher. In this way, generation of a single electron-hole pair, following upon absorption of a photon impinging upon the SPAD, is sufficient to trigger an ionization process that causes an avalanche multiplication of the carriers, with gains of the order of $10^6$ and consequent generation in short times (hundreds of picoseconds) of the avalanche current. This avalanche current can be conveniently collected, typically by means of an external circuitry connected to the junction, for example by means of anode and cathode contacts, and forms an electrical signal at output from the SPAD.

The gain and the likelihood of detecting a photon, i.e., the sensitivity of the SPAD, are directly proportional to the value of reverse-biasing voltage $V_A$ applied to the SPAD. However, the fact that the reverse-biasing voltage $V_A$ is appreciably higher than the breakdown voltage $V_B$ means that the process of avalanche ionization, once triggered, is self-sustaining. Consequently, once triggered, the SPAD is no longer able to detect photons, with the consequence that, in the absence of appropriate remedies, the SPADs described manage to detect the arrival of a first photon, but not the arrival of subsequent photons. To be able to detect also these photons, it is necessary to quench the avalanche current generated within the SPAD, arresting the process of avalanche ionization. In practice, it is necessary to reduce, for a period of time known as "hold-off time", the effective voltage $V_e$ across the junction, this effective voltage $V_e$ coinciding with the reverse-biasing voltage $V_A$ only in the absence of photons, i.e., in the absence of current within the SPAD. In this way, the ionization process is inhibited, and the avalanche current is quenched. Next, the initial conditions of biasing of the junction are restored in such a way that the SPAD is again able to detect photons.

In order to reduce the effective voltage $V_e$ across the junction subsequent to absorption of a photon, SPADs adopt the so-called "quenching circuits", either of an active type or of a passive type.

Irrespective of the details of implementation of the SPAD, and thanks to the use of the latter, the diagnostic system described in the patent application No. WO2007/144864 is characterized by a high sensitivity; however, it calls for particular care in use. The diagnostic system is operated as shown in FIGS. 1a and 1b.

Figure 1A:
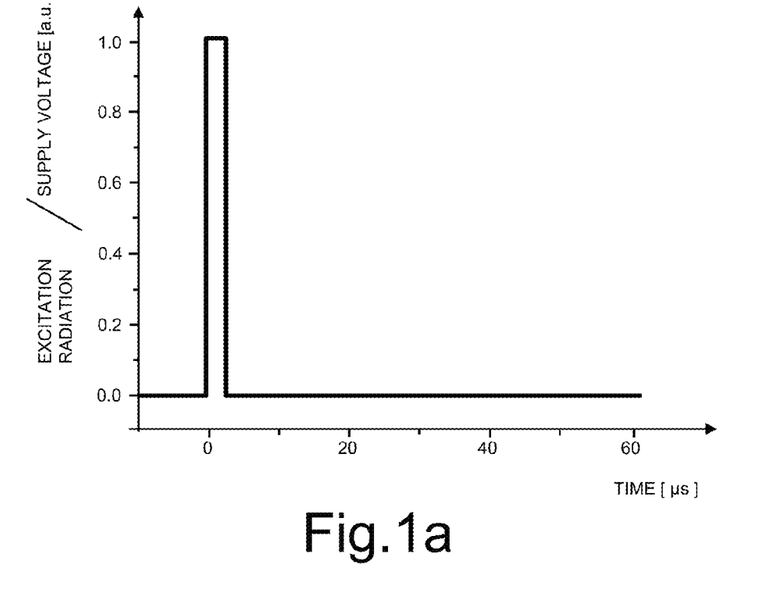
FIG. 1a shows a time plot of a signal for driving an optical source, expressed in arbitrary units, or, equivalently, a time plot of the intensity of the electromagnetic radiation emitted by the optical source.
Figure 1B:
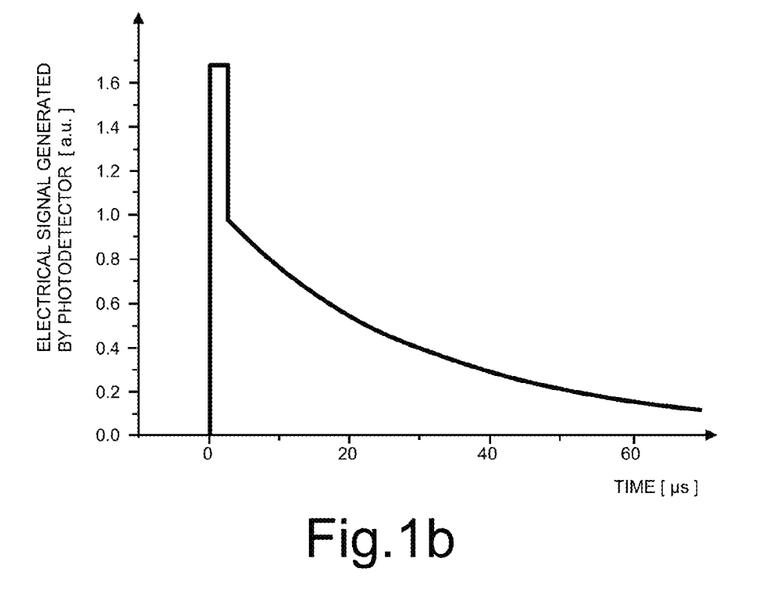
FIG. 1b shows a time plot of an electrical signal generated by an optical detector, expressed in arbitrary units.

In particular, as shown in FIG. 1a, the optical source operates in pulsed regime; i.e., it generates pulses of the excitation radiation, each pulse having a duration for example in the region of a few microseconds. Purely by way of example, FIG. 1a plots a supply voltage of the optical source; hence, this is also indicative of the intensity of the excitation radiation emitted by the optical source.

Considering a single pulse of the excitation radiation, and in the case of presence of activated markers in the detection region, they are excited by this pulse and emit light radiation at the wavelength $\lambda_f$. If the radiation emitted by the activated markers and excited is referred to as "optical response signal", this decays exponentially in time, with a time constant comprised between a microsecond and a few milliseconds.

In detail, the geometry of the diagnostic system described in the patent application No. WO2007/144864 is such that, if the optical signal to be detected is referred to as "optical signal that impinges upon the optical detector", this is formed both by the excitation radiation and by the optical response signal emitted by the activated markers.

After the optical detector has been impinged upon by the optical signal to be detected, it generates an electrical signal of the type shown in FIG. 1b. In particular, the electrical signal has a first portion and a second portion, which follow one another in time and correspond, respectively, to a first portion and a second portion of the optical signal to be detected.

The first portion of the optical signal to be detected is due principally to the pulse generated by the optical source, whilst the second portion is caused by the light radiation emitted by the activated markers and excited and consequently has a decreasing-exponential evolution.

This being said, during the first portion of the optical signal to be detected, the latter has an intensity such as to cause a sort of blinding of the optical detector; i.e., it causes saturation thereof. In other words, the first portion of the electrical signal is characterized by a high intensity, which is substantially independent of the number of activated markers and hence does not contain information useful for diagnostic purposes. Consequently, the optical detector is controlled in such a way that only the second portion of the electrical signal generated thereby is effectively processed for diagnostic purposes.

This modality of control of the optical source and of the optical detector hence exploits the so-called "phenomenon of delayed fluorescence" and enables benefiting from the advantages associated to the use of the SPAD, and moreover does not require a narrow-band optical filter having the function of filtering the excitation radiation to be set between the specimen to be analysed and the optical detector. However, in order to excite as many markers as possible, the intensity of the pulses of the excitation radiation is particularly high. Consequently, these pulses cause, once received by the SPAD, formation of a large number of electrical carriers within the semiconductor body that forms the SPAD itself. In turn, the electrical carriers cause an increase in the so-called "dark noise".

In detail, the SPAD operates in a way such as to determine, for each time interval, a corresponding count, i.e., a corresponding number of photons received thereby during said time interval. This being said, the aforementioned electrical carriers cause an increase in the so-called dark counts, namely, counts that are in any case determined by the SPAD in the absence of the optical signal to be detected. In practice, the electrical carriers hence lead to an increase of the count supplied by the SPAD as compared to the photons effectively received during the time interval.

In greater detail, the increase in dark counts occurs not only in coincidence with reception of the pulse, i.e., during the aforementioned first portion of the optical signal to be detected, but continues even after the pulse is exhausted; i.e., it continues even during the aforementioned second portion of the optical signal to be detected.

Figure 2A:
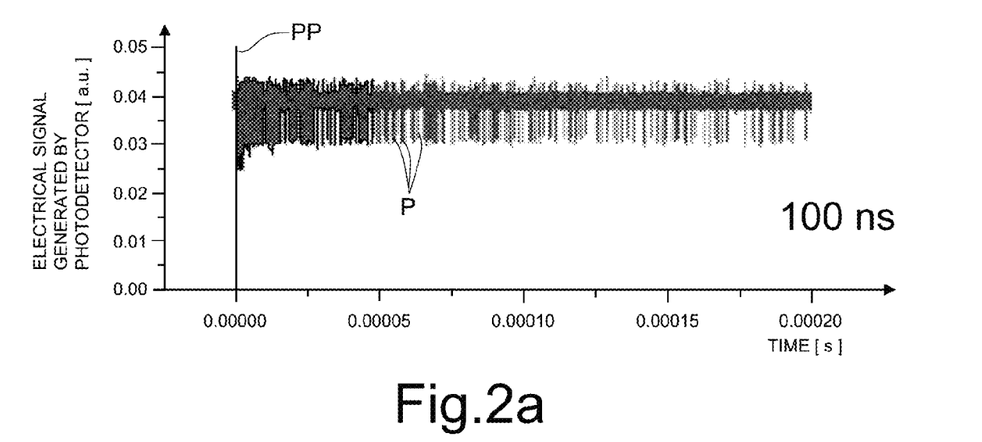
FIGS. 2a-2c show time plots of electrical signals at output from a SPAD, respectively in the case of excitation with optical pulses having a time duration of 100 ns and 2 ns, and in the case of absence of excitation.
Figure 2B:
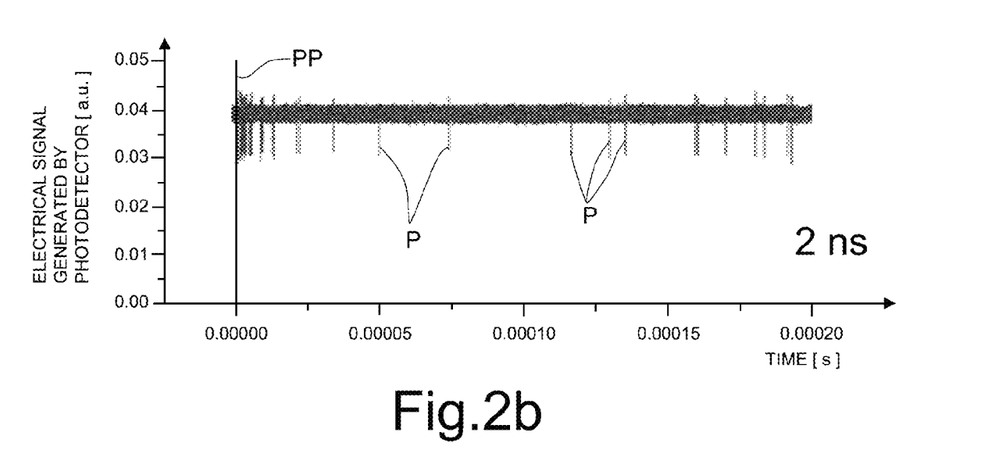
Figure 2C:
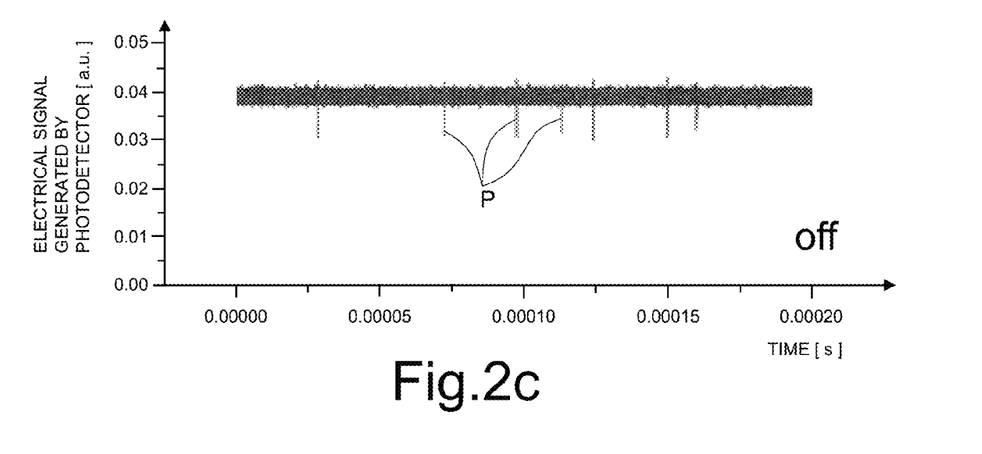

Purely by way of example, FIGS. 2a-2c show the time plot of the electrical signal at output from the SPAD, on the hypothesis of absence of activated markers. Moreover, FIGS. 2a and 2b refer to the cases of pulses having equal intensity and duration respectively of 100 ns and 2 ns, whilst FIG. 2c regards the case of absence of pulses. In practice, the plot shown in FIG. 2c has a certain number of peaks P per unit time, this number being indicative of the intrinsic "dark noise" of the SPAD. The plots shown in FIGS. 2b and, above all, 2a show, instead, an increase of the number of peaks P per unit time. In each of these two cases, this increase is due to the reception, by the SPAD, of a corresponding pulse PP generated by the optical source.

The increase in the dark noise is proportional to the energy of the pulses and can hence be contained by means of limitation of the latter, but this entails a reduction of the number of activated markers that are effectively excited.

The aim of the present invention is to provide a diagnostic device that will enable the drawbacks of the known art to be overcome at least in part.

SUMMARY

In one aspect, certain embodiments described herein relate to a diagnostic device. The diagnostic device comprises: a photodiode formed in a body of semiconductor material having a first surface; an integrated optical structure arranged on the first surface and having a second surface, the integrated optical structure including at least a first layer of a first material and a second layer of a second material, wherein the first layer defines the second surface; and at least one detection region arranged on the second surface, the at least one detection region comprising a receptor configured to bind to a corresponding target molecule of a specimen to be analysed, such that the binding is detectable by exciting a marker, which, when excited by electromagnetic radiation having a first wavelength ($\lambda_e$), emits electromagnetic radiation having a second wavelength ($\lambda_f$) that can be detected by the photodiode; wherein the first material has a first refractive index ($n_1$) and the first layer has a thickness substantially equal to an integer and odd multiple of one fourth of the first wavelength ($\lambda_e$) divided by the first refractive index ($n_1$).

In another aspect, certain embodiments described herein relate to a diagnostic system. The diagnostic system comprises: at least one diagnostic device and an optical source for illuminating the at least one diagnostic device with electromagnetic radiation having the first wavelength ($\lambda_e$).

In yet another aspect, certain embodiments described herein relate to a diagnostic method. The method comprises: illuminating at least one diagnostic device with electromagnetic radiation having the first wavelength ($\lambda_e$); biasing the junction of at least one avalanche photodiode in the at least one diagnostic device at a reverse-biasing voltage higher, in modulus, than the breakdown voltage ($V_B$); and generating at least one avalanche current in the at least one avalanche photodiode.

BRIEF DESCRIPTION OF THE DRAWINGS

Embodiments are described herein purely by way of non-limiting example and with reference to the attached drawings, wherein.

DETAILED DESCRIPTION

Figure 3:
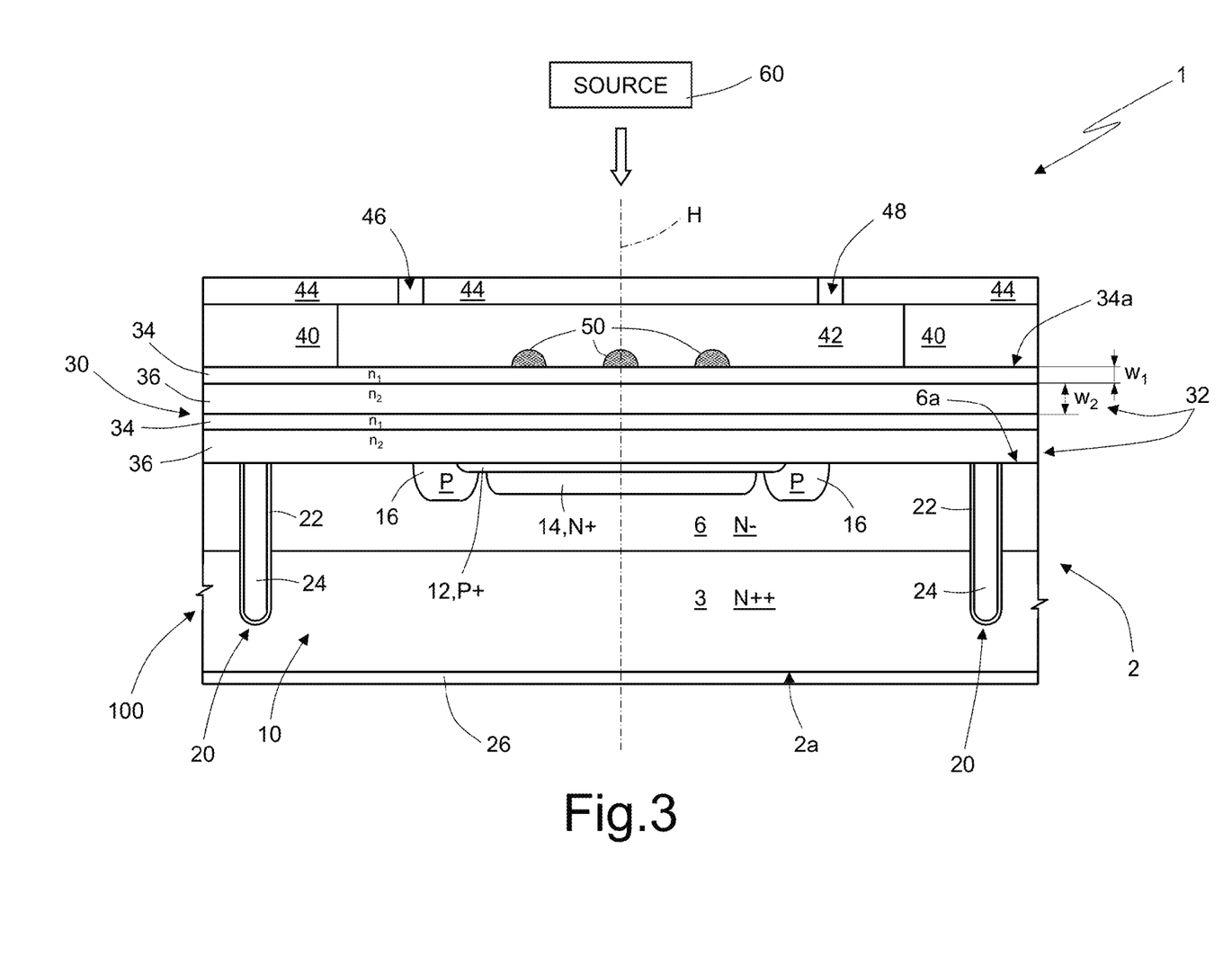
FIGS. 3 and 7 are schematic cross sections of embodiments of the present diagnostic device.

FIG. 3 shows a diagnostic device 1, which comprises a SPAD 2, referred to hereinafter, for brevity, as photodiode 2. In detail, the photodiode 2 is integrated in a chip 100 that includes a substrate 3 of semiconductor material, of an N++ type and having a bottom surface 2a. Moreover, the photodiode 2 includes an epitaxial layer 6. The epitaxial layer 6 is of an N− type and overlies the substrate 3 in direct contact therewith; moreover, the epitaxial layer 6 has a top surface 6a.

The substrate 3 and the epitaxial layer 6 form in practice a body 10 of semiconductor material, which has an axis H perpendicular to the top surface 6a and to the bottom surface 2a. Moreover, purely by way of example, the doping level of the substrate 3 is higher by three orders of magnitude than the doping level of the epitaxial layer 6.

An anode region 12, of a P+ type and circular or polygonal (for example, quadrangular) in shape, faces the top surface 6a and extends within the epitaxial layer 6.

An enriched region 14, of an N+ type, extends in the epitaxial layer 6, underneath, and in direct contact with, the anode region 12. In top plan view, the enriched region 14 is circular or polygonal (for example, quadrangular) in shape. The doping level of the enriched region 14 is higher than the doping level of the epitaxial layer 6.

For practical purposes, the anode region 12 and the enriched region 14 form a PN junction, designed to receive photons and to generate the avalanche current. The enriched region 14 and the epitaxial layer 6 have, instead, the purpose of confining a high electrical field in the proximity of the PN junction, reducing the breakdown voltage $V_B$ of the junction itself.

A circular guard ring 16, of a P type, extends in the epitaxial layer 6. In particular, the guard ring 16 faces the top surface 6a and is arranged on the outside of, and contiguous to, the anode region 12. The guard ring 16 forms a PN diode with the epitaxial layer 6 so as to prevent the so-called "edge breakdown" of the anode region 12.

The photodiode 2 further comprises a lateral insulation region 20, arranged outside the guard ring 16; moreover, the lateral insulation region 20 extends from the top surface 6a and in part into the substrate 3.

The lateral insulation region 20 comprises a channel-stopper region 22, which is arranged more externally, is made of dielectric material (for example, oxide) and is in direct contact with the substrate 3 and with the epitaxial layer 6. Furthermore, the lateral insulation region 20 comprises a metal region 24, which fills the channel-stopper region 22, by which it is surrounded.

In a way in itself known, the photodiode 2 further comprises an anode metallization (not shown), which is in direct contact with the guard ring 16, and a cathode metallization 26, which extends underneath the bottom surface 2a of the substrate 3. The anode and cathode metallizations enable biasing of the PN junction with a reverse-biasing voltage $V_A$ higher, in modulus, than the breakdown voltage $V_B$ of the PN junction itself.

For practical purposes, the enriched region 14, the epitaxial layer 6, and the substrate 3 form a cathode region. As regards, instead, the lateral insulation region 20, it enables, by means of the metal region 24, optical insulation of the photodiode 2 from possible other photodiodes formed in the same chip 100. Moreover, the channel stopper 22 guarantees electrical insulation of the photodiode 2 from said possible other photodiodes.

Arranged on the top surface 6a is a Bragg grating 30, which is made, for example, of two pairs of grating layers 32, each pair of grating layers 32 being formed by a first grating layer 34 and a second grating layer 36, made of materials having different refractive indices. In particular, the first and second grating layers 34, 36 are made, respectively, of a first material and a second material, which have, respectively, refractive indices $n_1$ and refractive index $n_2$, as well as thicknesses $w_1$ and $w_2$. For example, the first and second materials may be made of silicon dioxide $SiO_2$ and titanium dioxide $TiO_2$, respectively; in general, the first and second materials are dielectric and are transparent to the fluorescence wavelength $\lambda_f$.

In greater detail, within each pair of grating layers 32, the first grating layer 34 overlies the second grating layer 36, with which it is in direct contact. Hence it occurs that, if the pair of grating layers closer to the top surface 6a is referred to as "first pair of grating layers", the second grating layer of the first pair of grating layers is in contact with the top surface 6a. Moreover, we have $n_1<n_2$, for the reasons described hereinafter.

Arranged on top of the Bragg grating 30, and in particular on top of the first grating layer of the second pair of grating layers, is a structural layer 40, formed inside which is a channel 42, obtained by selective removal of portions of the structural layer 40 until the underlying Bragg grating 30 is reached and exposed. Consequently, the channel 42 is delimited laterally by the structural layer 40; moreover, the channel 42 is delimited at the bottom by an intermediate surface 34a, which is defined by the first grating layer of the second pair of grating layers.

Arranged on top of the structural layer 40 is a cover layer 44, which delimits the channel 42 at the top.

The channel 42 can be accessible to a specimen to be analysed of a fluid type, for example by providing a first opening 46 and a second opening 48 within the cover layer 44. Moreover, formed within the channel 42 is at least one detection region 50, of a type in itself known and arranged on top of the intermediate surface 34a, with which it is in direct contact. Purely by way of example, in FIG. 3 three detection regions 50 are shown.

Figure 4:
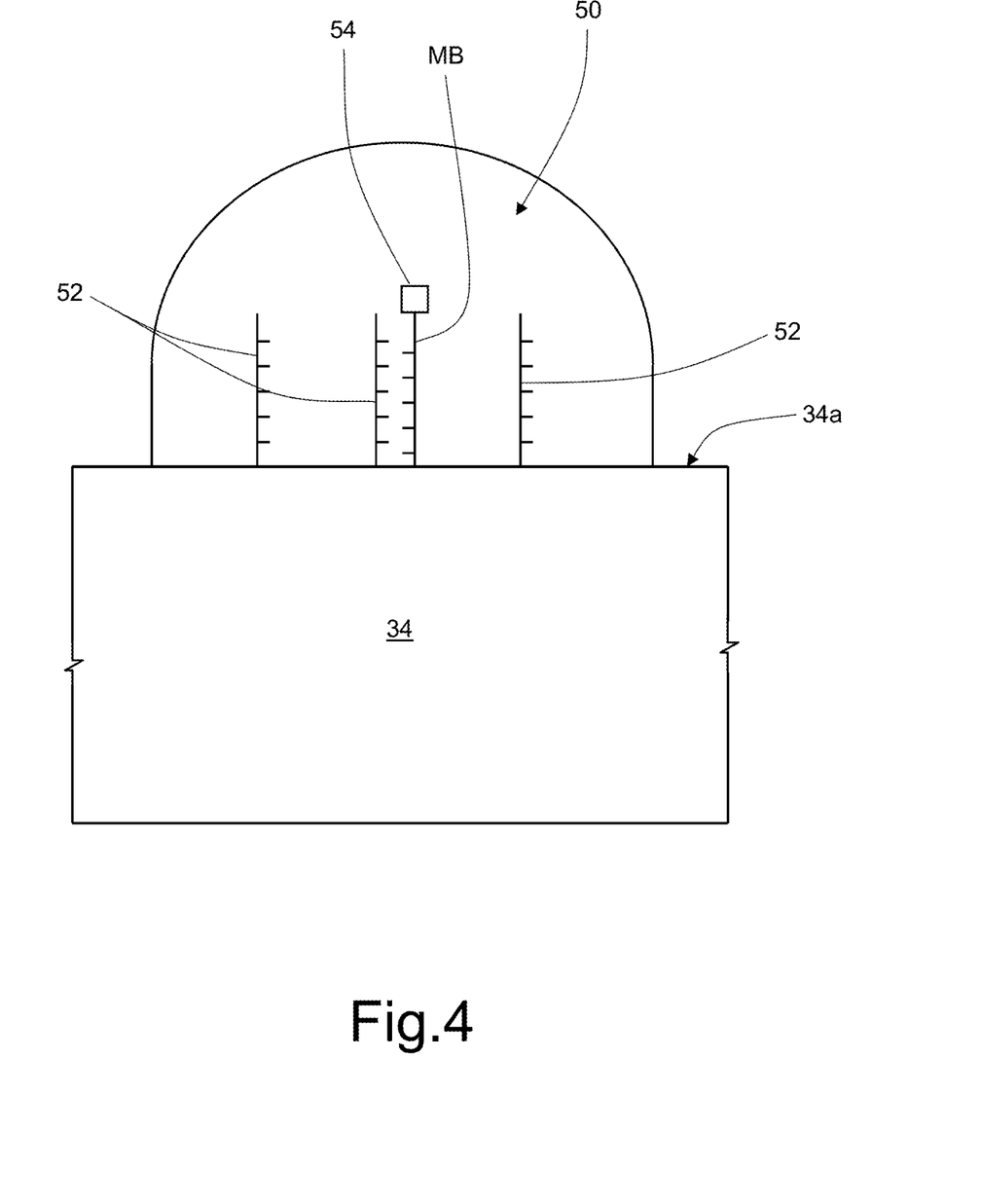
FIG. 4 is a schematic cross section of a portion of the diagnostic device shown in FIG. 3.

As shown in FIG. 4, each detection region 50 is formed, for example, by drops of biological material, present inside which are receptors 52, which are, for example, immobilized on the intermediate surface 34a.

By getting the detection regions 50 to come into contact with the specimen to be analysed there can be set bonds between the receptors 52 and target molecules MB present in the specimen to be analysed that flows in the channel 42. It is thus possible to get the markers 54 of a fluorescent (or phosphorescent) type to be activated, i.e., to mate with the target molecules MB that have bound to the receptors 52 in such a way that these markers 54 label the receptors 52 themselves. For this purpose, and purely by way of example, the markers 54 can be originally present in a marker fluid, which is caused to flow in the channel 42 after the specimen to be analysed has been caused to flow in the channel 42.

Arranged on top of the diagnostic device 1 is an optical source 60, designed to generate excitation radiation at the excitation wavelength $\lambda_e$, the cover layer 44 being transparent to the wavelength $\lambda_e$. The markers 54 are of the type such that, when activated and excited by radiation at the excitation wavelength $\lambda_e$, emit radiation at a fluorescence wavelength $\lambda_f$, which is detected by the underlying photodiode 2. For this purpose, the first and second materials are transparent to the fluorescence wavelength $\lambda_f$.

This being said, thanks to the presence of the Bragg grating 30, there is an increase in the electrical field associated to the excitation radiation, at the intermediate surface 34a, and hence in the proximity of the detection regions 50, with consequent increase in excitation of the markers and, hence, in the radiation at the fluorescence wavelength $\lambda_f$. This is due to phenomena of interference that arise within the Bragg grating 30, where the thicknesses $w_1$ and $w_2$ of the first grating layer 34 and the second grating layer 36 of each pair of grating layers 32 are, respectively, equal to an integer and odd multiple of $\lambda_e/(4 \cdot n_1)$ and $\lambda_e/(4 \cdot n_2)$, hence having assumed that the excitation radiation has a propagation vector parallel to the axis H.

Figure 5:
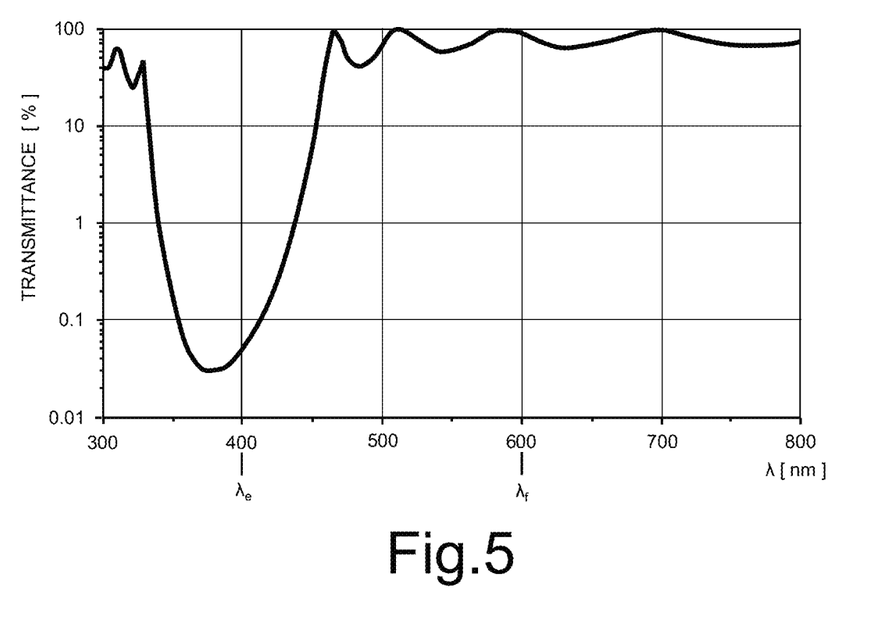
FIGS. 5 and 8 show plots of the transmittance of optical structures formed in embodiments of the present diagnostic device, as a function of the wavelength.

At the same time, the presence of the Bragg grating 30 entails a reduction of the fraction of excitation radiation that passes beyond the top surface 6a, which, as explained previously, can cause an increase in the dark noise of the photodiode 2. This is due to the fact that, as shown purely by way of example in FIG. 5, where it is assumed that $\lambda_e=400$ nm $\lambda_f=600$ nm, the Bragg grating 30 has a transmittance that has a minimum in the proximity of the excitation wavelength $\lambda_e$. In addition, the transmittance has a maximum in the proximity of the fluorescence wavelength $\lambda_f$, or in any case it is found that the ratio between the transmittance at the fluorescence wavelength $\lambda_f$ and at the excitation wavelength $\lambda_e$ is higher than ten.

Figure 6:
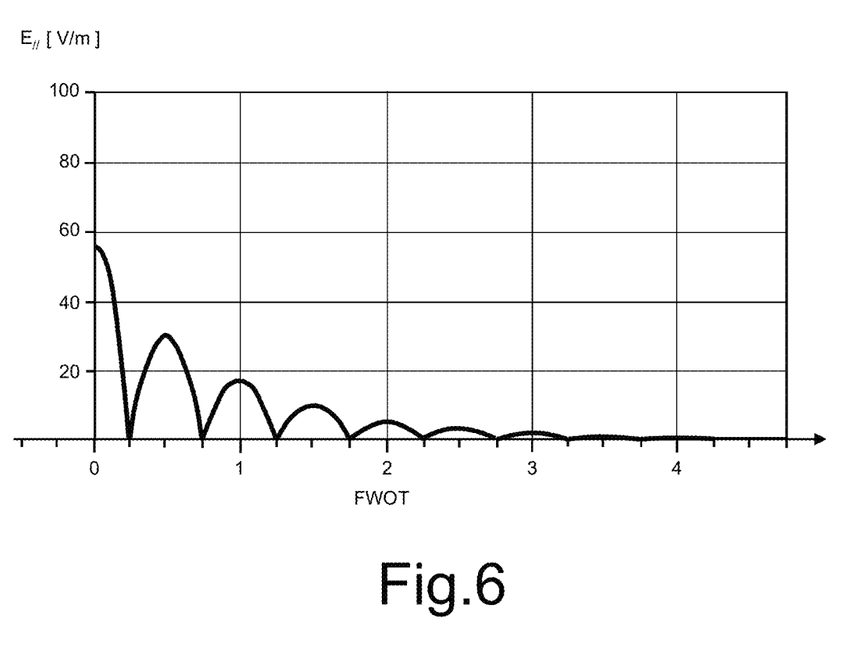
FIG. 6 shows the plot of a component of the electrical field within a portion of an embodiment of the present diagnostic device.

Purely by way of example, FIG. 6 shows qualitatively the plot of the parallel component of the electrical field associated to the excitation radiation, i.e., the component parallel to the intermediate surface 34a. In particular, FIG. 6 regards an embodiment in which the Bragg grating 30 is formed by nineteen pairs of grating layers; moreover, the axis of the abscissae shown in FIG. 6 is expressed in terms of the full-wave optical thickness (FWOT).

In any case, possible are embodiments in which the Bragg grating 30 has a different number of pairs of grating layers.

Figure 7:
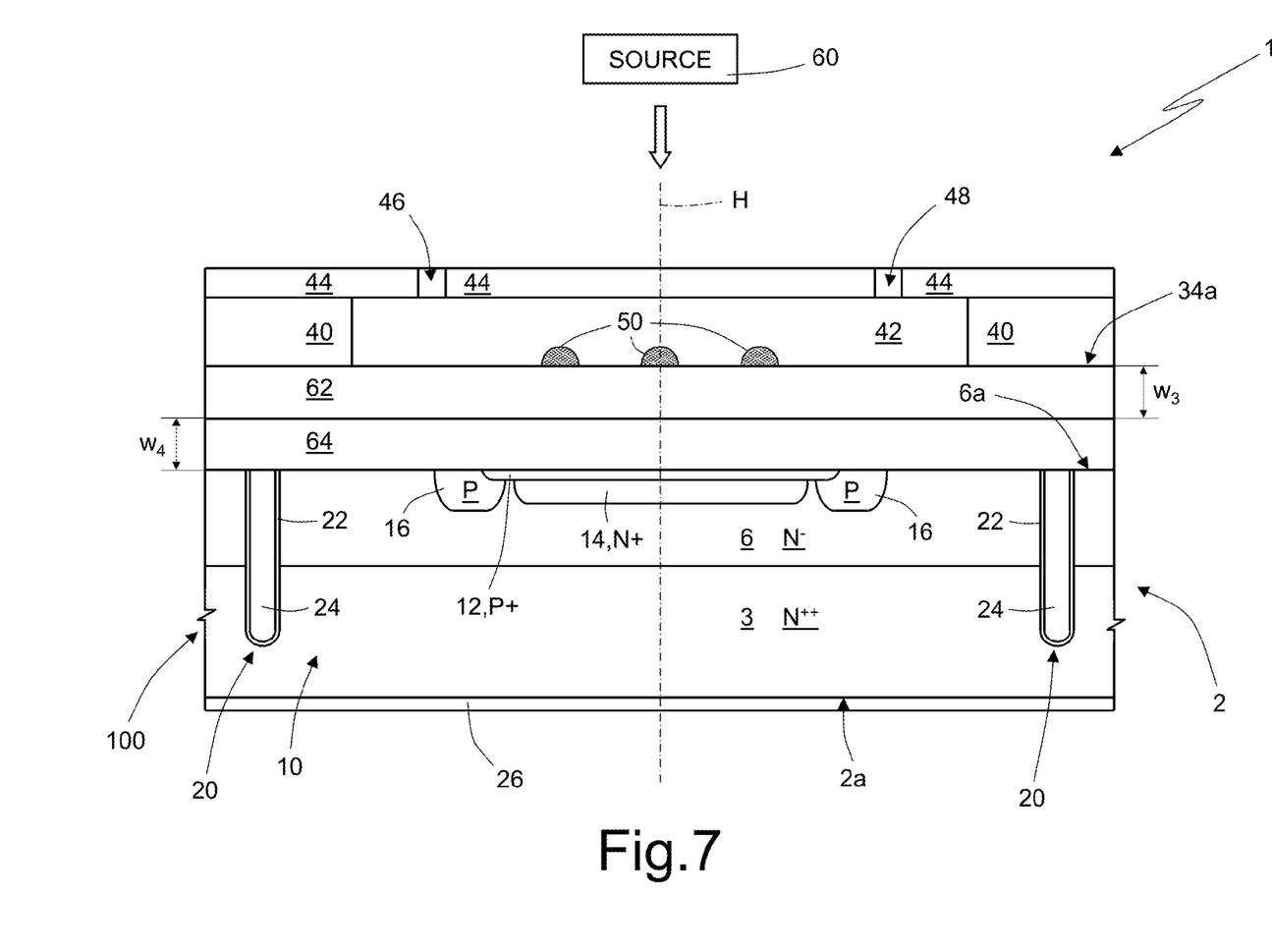

Moreover possible are embodiments of the type shown in FIG. 7, where, instead of the Bragg grating 30, a reflecting layer 62 and an additional region 64 are present.

In particular, the additional region 64 extends over the top surface 6a. The reflecting layer 62 extends over the additional region 64 and forms the intermediate surface 34a. The reflecting layer 62 and the additional region 64 have thicknesses equal, respectively, to $w_3$ and $w_4$; moreover, $w_3$ is an integer and odd multiple of $\lambda_e/4$ in order to increase the electrical field associated to the excitation radiation, in the detection regions 50.

For example, the reflecting layer 62 and the additional region 64 can be formed, respectively, by silicon dioxide $SiO_2$ and by amorphous silicon, the latter being deposited directly on the anode region 12 of the photodiode 2. The additional region 64 has an absorption coefficient at the excitation wavelength $\lambda_e$ higher than the absorption coefficient at the fluorescence wavelength $\lambda_f$.

Figure 8:
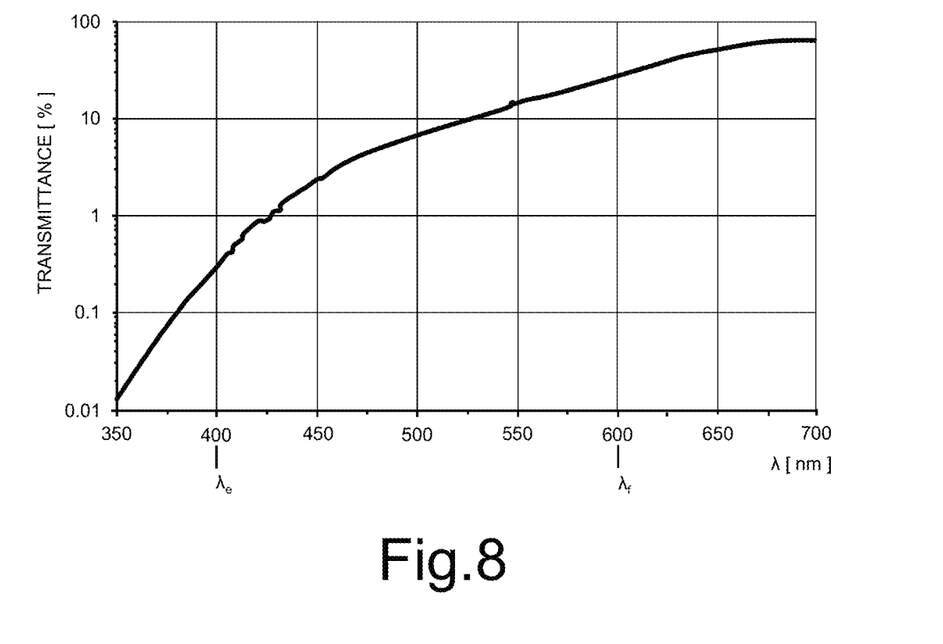

In practice, the reflecting layer 62 and the additional region 64 form an optical structure, the transmittance of which has a plot, as a function of the wavelength, of the type shown in FIG. 8. This plot is of a monotonic type; moreover, the value of transmittance at the excitation wavelength $\lambda_e$ is less than the value of transmittance at the fluorescence wavelength $\lambda_f$, with consequent reduction of the impact that the excitation radiation has on the dark noise of the photodiode 2 as compared to the case of absence of the reflecting layer 62 and of the additional region 64.

Figure 9:
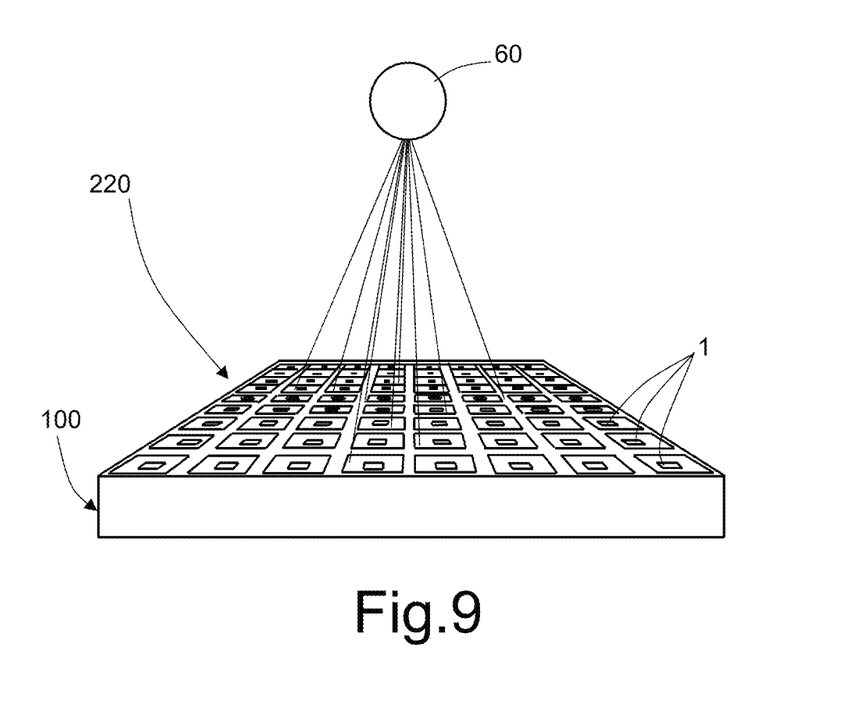
FIG. 9 is a schematic perspective view of an array of diagnostic devices, coupled to a light source.

As shown in FIG. 9, the diagnostic device 1 can belong to an array 220 of diagnostic devices 1, formed in the chip 100. The array 220 can comprise any number of diagnostic devices, according to the need.

In practice, formed in the chip 100 is a planar array of SPADs, grown on one and the same substrate. This planar array defines a so-called "silicon photomultiplier" (SiPM). In detail, the anode and cathode metallizations of the SPADs are configured so that they can be all connected to a single voltage generator.

Consequently, the SPADs of the SiPM can be biased to one and the same reverse-biasing voltage $V_A$; moreover, the avalanche currents generated within the SPADs are multiplexed together so as to generate an output signal of the SiPM equal to the summation of the output signals of the SPADs. The SiPM is hence a device with large area and high gain, capable of supplying, on average, an electrical output signal (current) proportional to the number of photons that impinge upon the SiPM. In fact, each SPAD of the SiPM behaves like an independent binary counter, and the output signal of the SiPM is proportional to the number of SPADs in which the process of avalanche ionization (detection of a photon) is triggered, this number being in turn proportional to the number of incident photons.

Figure 10:
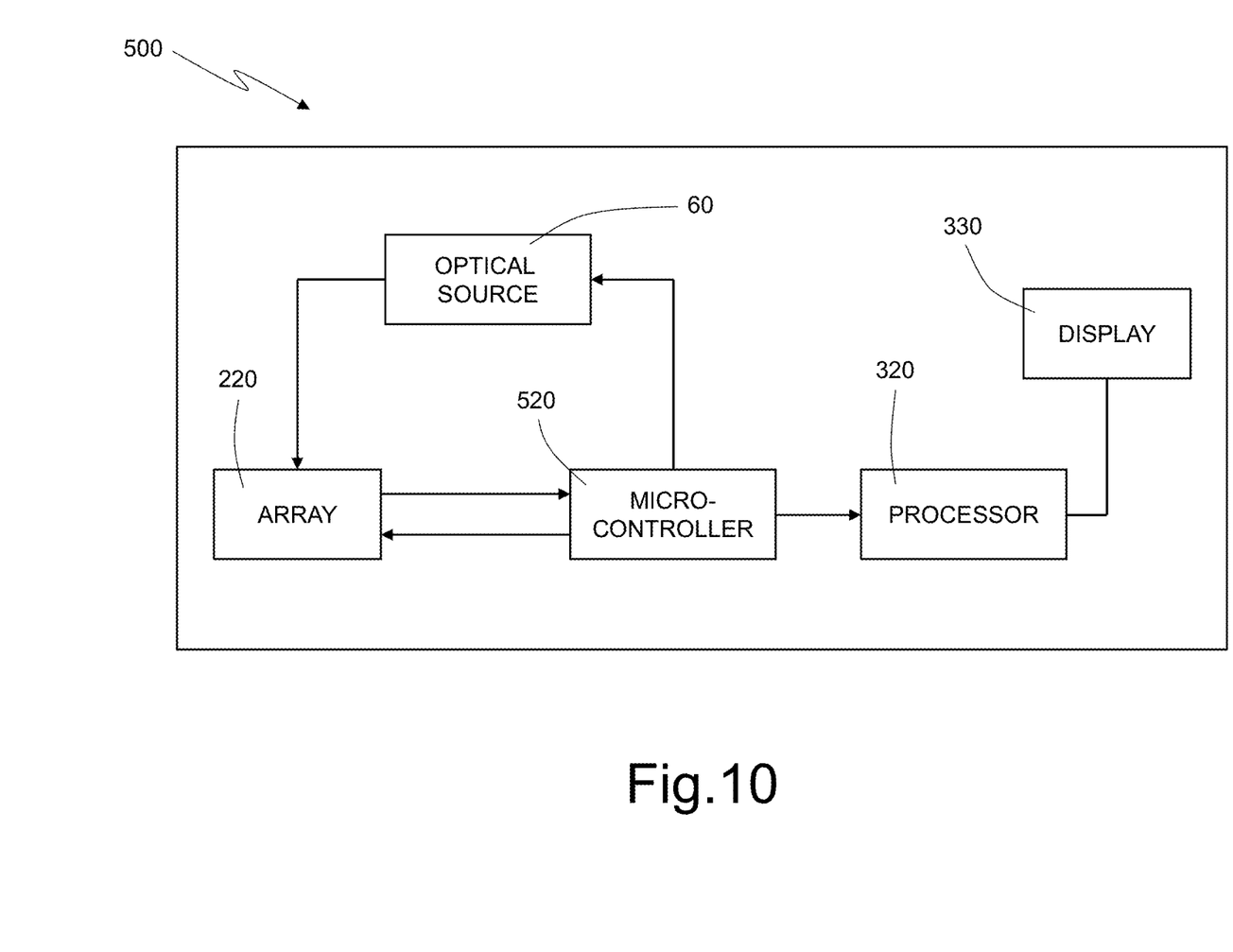
FIG. 10 shows a block diagram of a diagnostic system including the array shown in FIG. 9.

The array 220 can be used in a generic diagnostic system 500 as shown in FIG. 10, where the optical source 60 illuminates an array 220 of diagnostic devices and is controlled by a microcontroller unit 520, which is moreover connected to the array 220. The microcontroller unit 520 processes the output signal of the array 220 and supplies a processed signal to a processor 320, which enables analysis of the processed signal and display of the information associated to the processed signal on a display 330.

The advantages that the present diagnostic device affords emerge clearly from the foregoing discussion. In particular, the present diagnostic device makes it possible to benefit from the high sensitivity of SPADs and the so-called "delayed fluorescence", without incurring in the increase of dark noise caused by the pulses of the excitation radiation.

Finally, it is evident that modifications and variations may be made to the diagnostic device described herein, without thereby departing from the scope of the present invention.

For example, the specific markers can be phosphorescence markers, instead of fluorescence markers. Furthermore, the channel can be of a different type from the one shown; in particular, it is not necessary for the channel to be designed to enable flow of the specimen, i.e., to be of the so-called "microfluidic" type.

It is moreover possible, in principle, that the photodiode is not of a SPAD type since a reduction of the dark noise is obtained also in the case of different photodiodes. In addition, as regards the SPAD, the types of doping of the anode region, the enriched region, the substrate, and the epitaxial layer may be reversed.

Finally, the mechanisms of binding of the receptors, of the target molecules, and of the markers may be different from the ones described. For instance, in a way in itself known, the markers may be already present in the specimen to be analysed, in which case they are already bound to the target molecules, which subsequently bind with the receptors. In general, in any case, we refer to "activated markers" in order to refer to the markers coupled to the receptors by mating to the target molecules, irrespective of the details of implementation that have brought about said mating.

The invention claimed is:

1. A diagnostic device comprising:
    a photodiode formed in a body of semiconductor material having a first surface;
    an integrated optical structure arranged on the first surface and having a second surface, the integrated optical structure including:
        a first layer of a first material that has a first refractive index, the first layer defining the second surface and having a first thickness that is substantially equal to an integer and odd multiple of one fourth of a first wavelength divided by the first refractive index; and
        a second layer of a second material, the second layer being in direct contact with the first layer and arranged between the first layer and the body of semiconductor material, the second material having a second refractive index that is greater than the first refractive index, the second layer having a second thickness that is substantially equal to an integer and odd multiple of one fourth of the first wavelength divided by the second refractive index; and
    a detection region arranged on the second surface, the detection region including a receptor that, when contacted with a specimen to be analysed, binds to a corresponding target molecule of the specimen to be analysed, such that the binding is detectable by exciting a marker, which, when excited by electromagnetic radiation having the first wavelength, emits electromagnetic radiation having a second wavelength that can be detected by the photodiode.

2. The diagnostic device according to claim 1, wherein the first material is silicon dioxide and the second material is titanium dioxide.

3. The diagnostic device according to claim 1, wherein the integrated optical structure forms a Bragg grating.

4. The diagnostic device according to claim 3, wherein the Bragg grating includes a plurality of layers of the first material and a plurality of layers of the second material.

5. The diagnostic device according to claim 3, wherein the Bragg grating has a first transmittance at the first wavelength and has a second transmittance at the second wavelength, and wherein a ratio between the second transmittance and the first transmittance is greater than ten.

6. The diagnostic device according to claim 1, wherein the second layer has a first absorption coefficient at the first wavelength and a second absorption coefficient at the second wavelength, the first absorption coefficient being higher than the second absorption coefficient.

7. The diagnostic device according to claim 6, wherein the first material is silicon dioxide and the second material is amorphous silicon.

8. The diagnostic device according to claim 1, wherein the photodiode is an avalanche photodiode operable in Geiger mode.

9. The diagnostic device according to claim 8, wherein the body of semiconductor material has a cathode region and the avalanche photodiode has an anode region extending within the body of semiconductor material on top of the cathode region and facing the first surface, wherein the anode and cathode regions form a junction that has a breakdown voltage and can be biased at a reverse-biasing voltage higher, in modulus, than the breakdown voltage.

10. The diagnostic device according to claim 9, wherein the body of semiconductor material comprises a substrate, an epitaxial layer, and an enriched region, the enriched region extending within the epitaxial layer and underneath the anode region, and having a doping level higher than that of the epitaxial layer.

11. The diagnostic device according to claim 1, wherein the marker is a fluorescence marker.

12. The diagnostic device according to claim 1, further comprising a structural layer on the integrated optical structure, wherein a channel is defined by the structural layer and the second surface of the integrated optical structure, and wherein the detection region is within the channel.

13. A diagnostic system comprising:
a first diagnostic device that includes:
a first photodiode formed in a body of semiconductor material having a first surface;
a first integrated optical structure arranged on the first surface and having a second surface, the first integrated optical structure including a first layer of a first material and a second layer of a second material, wherein the first layer defines the second surface, wherein the first material has a first refractive index and the first layer has a thickness substantially equal to an integer and odd multiple of one fourth of the first wavelength divided by the first refractive index; and
a first detection region arranged on the second surface, the first detection region including a first receptor that, when contacted with a specimen to be analysed, binds to a corresponding first target molecule of the specimen to be analysed, such that the binding of the first receptor and the corresponding first target molecule is detectable by exciting a first marker, which, when excited by electromagnetic radiation having the first wavelength, emits electromagnetic radiation having a second wavelength that can be detected by the first photodiode; and an optical source that, in operation, illuminates the first diagnostic device with pulsed electromagnetic radiation having the first wavelength.

14. The diagnostic system according to claim 13, further comprising:
a semiconductor chip in which the first diagnostic device is formed; and
a second diagnostic device formed in the semiconductor chip and including:
a second photodiode formed in the body of semiconductor material;
a second integrated optical structure arranged on the first surface, the second integrated optical structure including a first layer of the first material and a second layer of the second material; and
a second detection region arranged on the second integrated optical structure, the second detection region including a second receptor that, when contacted with the specimen to be analysed, binds to a corresponding second target molecule of the specimen to be analysed, such that the binding of the second receptor and the corresponding second target molecule is detectable by exciting a second marker, which, when excited by electromagnetic radiation having the first wavelength, emits electromagnetic radiation having the second wavelength which can be detected by the second photodiode.

15. The diagnostic system according to claim 14, further comprising a processing unit electrically coupled to the semiconductor chip.

16. The diagnostic system according to claim 15, wherein the processing unit, when in operation, processes an output signal from the first and second diagnostic devices.

17. The diagnostic system according to claim 16, wherein the processing unit, when in operation, controls the optical source.

18. The diagnostic system according to claim 13, wherein the second layer is in direct contact with the first layer and is arranged between the first layer and the body of semiconductor material, the second material having a second refractive index that is greater than the first refractive index, the second layer having a second thickness that is substantially equal to an integer and odd multiple of one fourth of the first wavelength divided by the second refractive index.

19. A detection method comprising:
contacting a first detection region of a first diagnostic device with a specimen to be analysed, the first diagnostic device including:
a first avalanche photodiode operable in Geiger mode, the first avalanche photodiode being formed in a body of semiconductor material having a first surface, the body of semiconductor material having a first cathode region, and the first avalanche photodiode having a first anode region extending within the body of semiconductor material on top of the first cathode region and facing the first surface, the first anode region and the first cathode region forming a first junction that has a breakdown voltage and can be biased at a reverse-biasing voltage that is higher, in modulus, than the breakdown voltage;
a first integrated optical structure arranged on the first surface and having a second surface, the first integrated optical structure including:
a first layer of a first material having a first refractive index, the first layer defining the second surface and having a first thickness that is substantially equal to an integer and odd multiple of one fourth of a first wavelength divided by the first refractive index; and a second layer of a second material, the second layer being in direct contact with the first layer and arranged between the first layer and the body of semiconductor material, the second material having a second refractive index that is greater than the first refractive index, the second layer having a second thickness that is substantially equal to an integer and odd multiple of one fourth of the first wavelength divided by the second refractive index; and the first detection region arranged on the second surface, the first detection region including a first receptor that, when contacted with the specimen to be analysed, binds to a corresponding first target molecule of the specimen to be analysed, such that the binding of the first receptor and the corresponding first target molecule is detectable by exciting a marker, which, when contacted with the corresponding first target molecule, binds to the corresponding first target molecule and, when excited by electromagnetic radiation having the first wavelength, emits electromagnetic radiation having a second wavelength that can be detected by the first avalanche photodiode;

illuminating, with electromagnetic radiation having the first wavelength, the first diagnostic device;

biasing the first junction at the reverse-biasing voltage; and detecting a first avalanche current generated in the first avalanche photodiode, the first avalanche current being indicative of an amount of the corresponding first target molecule in the specimen to be analysed.

20. The detection method according to claim 19, further comprising:

contacting a second detection region of a second diagnostic device with the specimen to be analysed, the second diagnostic device being formed on a semiconductor chip in which the first diagnostic device is formed, the second diagnostic device including:

a second avalanche photodiode operable in Geiger mode, the second avalanche photodiode formed in the body of semiconductor material, which has a second cathode region, the second avalanche photodiode having a second anode region extending within the body of semiconductor material on top of the second cathode region and facing the first surface, the second anode region and the second cathode region forming a second junction that can be biased at the reverse-biasing voltage;

a second integrated optical structure arranged on the first surface, the second integrated optical structure including:

a first layer of the first material, the first layer having a third thickness that is substantially equal to an integer and odd multiple of one fourth of the first wavelength divided by the first refractive index; and a second layer of the second material, the second layer being in direct contact with the first layer and arranged between the first layer and the body of semiconductor material, the second layer having a fourth thickness that is substantially equal to an integer and odd multiple of one fourth of the first wavelength divided by the second refractive index; and the second detection region arranged on the second integrated optical structure, the second detection region including a second receptor that, when contacted with the specimen to be analysed, binds to a corresponding second target molecule of the specimen to be analysed, such that the binding of the second receptor and the corresponding second target molecule is detectable by exciting the marker, which, when excited by electromagnetic radiation having the first wavelength, emits electromagnetic radiation having the second wavelength which can be detected by the second avalanche photodiode;

illuminating, with the electromagnetic radiation having the first wavelength, the second diagnostic device;

biasing the second junction at the reverse-biasing voltage; and detecting a second avalanche current generated in the second avalanche photodiode, the second avalanche current being indicative of an amount of the corresponding second target molecule in the specimen to be analysed.

21. The detection method according to claim 1, further comprising:

multiplexing together the first avalanche current and the second avalanche current to generate an output signal; and processing, by a processor, the output signal.

* * * * *

UNITED STATES PATENT AND TRADEMARK OFFICE
CERTIFICATE OF CORRECTION

PATENT NO. : 9,658,158 B2  
APPLICATION NO. : 13/902468  
DATED : May 23, 2017  
INVENTOR(S) : Lucio Renna et al.

Page 1 of 1

It is certified that error appears in the above-identified patent and that said Letters Patent is hereby corrected as shown below:

In the Claims

Column 14, Lines 42-43:
"21. The detection method according to claim 1, further comprising:" should read, --21. The detection method according to claim 20, further comprising:--.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*